United States Patent
Achkar et al.

(10) Patent No.: US 9,841,424 B2
(45) Date of Patent: Dec. 12, 2017

(54) SEROLOGIC TEST FOR THE RAPID DIAGNOSIS OF ACTIVE TUBERCULOSIS

(71) Applicant: ALBERT EINSTEIN COLLEGE OF MEDICINE OF YESHIVA UNIVERSITY, Bronx, NY (US)

(72) Inventors: Jacqueline Michele Achkar, Brooklyn, NY (US); Arturo Casadevall, New York, NY (US); Rafael Prados-Rosales, New York, NY (US); Anke Ziegenbalg, Stoney Brook, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 14/434,415

(22) PCT Filed: Oct. 10, 2013

(86) PCT No.: PCT/US2013/064203
§ 371 (c)(1),
(2) Date: Apr. 9, 2015

(87) PCT Pub. No.: WO2014/059065
PCT Pub. Date: Apr. 17, 2014

(65) Prior Publication Data
US 2015/0260714 A1  Sep. 17, 2015

Related U.S. Application Data

(60) Provisional application No. 61/713,158, filed on Oct. 12, 2012.

(51) Int. Cl.
*G01N 33/569* (2006.01)
*G01N 33/68* (2006.01)

(52) U.S. Cl.
CPC ..... *G01N 33/5695* (2013.01); *G01N 33/6854* (2013.01); *G01N 2333/35* (2013.01); *G01N 2469/20* (2013.01)

(58) Field of Classification Search
CPC ......... A61K 39/00; A61K 39/02; A61K 39/04
USPC ...... 424/184.1, 234.1, 248.1; 435/4, 7.1, 7.2
See application file for complete search history.

(56) References Cited

U.S. PATENT DOCUMENTS

2007/0212740 A1* 9/2007 Locht ................ G01N 33/5695
                                                435/7.32

OTHER PUBLICATIONS

PCT International Search Report and Written Opinion, dated Jan. 10, 2014 in connection with PCT International Application No. PCT/US2013/64203 11 pages.
Min F et al., entitled "Serum Antibody Responses to 10 *Mycobacterium tuberculosis* Proteins, Purified Protein Derivative, and Old Tuberculin in Natural and Experimental Tuberculosis in Rhesus Monkeys," Clinical and Vaccine Immunology, Dec. 2011, vol. 18, No. 12, pp. 2154-2160.
Sun Z et al., entitled "Mycobacterial heparin-binding haemagglutinin adhesion-induced interferon & antibody for detection of tuberculosis," Indian J Med Res 133, Apr. 2011, pp. 421-425.
He X Y et al., entitled "Assessment of Five Antigens from *Mycobacterium tuberculosis* for Serodiagnosis of Tuberculosis," Clinical and Vaccine Immunology, Apr. 2011, vol. 18, No. 4, pp. 565-570.
Shin A-R et al., entitled "*Mycobacterium tuberculosis* HBHA Protein Reacts Strongly with the Serum Immunoglobulin M of Tuberculosis Patients," Clinical and Vaccine Immunology, Aug. 2006, vol. 13, No. 8, pp. 869-875.
Wu X et al., entitled "Comparison of antibody responses to seventeen antigens from *Mycobacterium tuberculosis*," Clinica Chimica Acta 411 (2010) pp. 1520-1528.

* cited by examiner

*Primary Examiner* — Gary Nickol
(74) *Attorney, Agent, or Firm* — Amster, Rothstein & Ebenstein LLP

(57) ABSTRACT

The present invention relates to methods and kits for detecting active tuberculosis infection in a subject using serological techniques and a first agent capable of binding an IgG, IgA and/or IgM directed to the first protein present in or on a *Mycobacterium tuberculosis* membrane vesicle or a *Bacillus* Calmette-Guerin (BCG) membrane vesicle. Also provided are methods of treating a subject with an active tuberculosis disease.

14 Claims, 6 Drawing Sheets

SEROLOGIC TEST FOR THE RAPID DIAGNOSIS OF ACTIVE TUBERCULOSIS

CROSS-REFERENCE TO RELATED APPLICATIONS

This application is a U.S. national stage entry under 35 U.S.C. §371 of PCT International Patent Application No. PCT/US2013/064203, filed on Oct. 10, 2013, which claims the benefit of U.S. Provisional Patent Application No. 61/713,158, filed on Oct. 12, 2012, the contents of all of which are hereby incorporated by reference.

BACKGROUND OF THE INVENTION

Throughout this application various publications are referred to by number in square brackets. Full citations for the references may be found at the end of the specification. The disclosures of each of these publications, and also the disclosures of all patents, patent application publications and books recited herein, are hereby incorporated by reference in their entirety into the subject application to more fully describe the art to which the subject invention pertains.

The disease tuberculosis (TB) remains a global public health problem. An estimated 8.8 million new cases occurred in 2010 with ~1.1 million TB-associated deaths among HIV– and ~0.35 million among HIV+ people [12]. Rapid TB diagnosis and treatment leads to reduced transmission, morbidity and mortality. However, diagnosis of TB is often delayed, especially in resource-limited settings where the vast majority of people with TB reside.

The clinical presentations of TB are manifold and diagnostic confirmation can be challenging. The gold standard test for TB diagnosis is detection of *Mycobacterium tuberculosis* (Mtb) in culture [13]. However, culture methods require laboratory infrastructure and have long turn-around-times of weeks to months. Molecular methods detecting Mtb-specific nucleic acids, especially the recently WHO endorsed GeneXpert MTB/RIF, have revolutionized the rapid diagnosis of drug-sensitive and resistant TB, but are costly and require technological investment [14-17]. Despite ongoing research to identify new biomarkers for TB, a simple cheap point of care (POC) test, applicable in all settings, is still not available [17, 18]. Therefore, although limited by a sensitivity of around 50% in detecting acid fast bacilli (AFB) in sputum smears [19-21], microscopy remains the most widely used method for rapid TB diagnosis, and often is the only test available in resource-limited settings.

Nevertheless, even microscopy requires collection and processing of at least 2 sputum samples, and it can take up to 2 days until results are available. Furthermore, these modalities require either sputum or another specimen from the site of disease, which may not be available. A novel urine antigen detection test for TB appears to have clinical value in patients with advanced HIV infection but not in HIV negative (HIV–) patients, which constitute a large portion of TB cases [22-25].

To complement the current armamentarium of diagnostic tests, TB biomarkers should be detectable in an easily accessible sample independent of the site of disease (e.g. blood or urine) and have the potential to be adapted into a rapid test requiring minimal to no laboratory infrastructure.

As another approach, the amplifying power of the immune responses can potentially detect infection with Mtb at a low antigen-threshold and distant from the site of infection. Assays that detect Mtb infection by measuring interferon gamma release of circulating lymphocytes in response to Mtb-specific antigens (IGRAs) are more accurate than the tuberculin skin test (TST) [26]. However, they require incubation of whole blood cells, which is not feasible in most resource-limited settings. More importantly, neither the TST nor IGRAs can distinguish TB from the asymptomatic state of infection, latent TB infection (LTBI) (reviewed in [27]). In contrast, assays detecting serum antibodies (Abs) can be scaled up into rapid, robust, inexpensive and simple formats requiring little laboratory infrastructure. Furthermore, it has been demonstrated that Ab responses to mycobacterial antigens can discriminate between TB and LTBI (reviewed in [28] and [29, 30]). However, commercially available serodiagnostic tests thus far are limited by insufficient sensitivity and specificity (reviewed in [5-7]). Given their poor performance, the WHO recently recommended against the use of commercial serodiagnostic tests, while encouraging further targeted research in this field [31].

The present invention addresses the need for improved rapid and simple tuberculosis disease assays.

SUMMARY OF THE INVENTION

A method is provided of detecting active Tuberculosis disease in a subject comprising contacting a sample from the subject with a first agent capable of binding an IgG, IgA and/or IgM directed to a first protein present in or on a *Mycobacterium tuberculosis* membrane vesicle or a *Bacillus* Calmette-Guérin (BCG) membrane vesicle, wherein detection of the presence of IgG, IgA and/or IgM directed to the first protein present in or on the membrane vesicle indicates an active Tuberculosis disease in the subject.

Also provided is a method of detecting active Tuberculosis disease in a subject comprising contacting a sample from the subject, wherein the sample has been treated so as to permit detection of the subject's antibodies to one or more proteins on a *Mycobacterium tuberculosis* membrane vesicle or *Bacillus* Calmette-Guérin (BCG) membrane vesicle, with a first agent capable of binding an IgG, IgA and/or IgM directed to a protein present in or on a *Mycobacterium tuberculosis* membrane vesicle or BCG membrane vesicle, and with a second agent capable of binding an IgG, IgA and/or IgM antibodies directed to a second protein present in or on a *Mycobacterium tuberculosis* membrane vesicle or BCG membrane vesicle, and with a third agent capable of binding an IgG, IgA and/or IgM directed to a third protein present in or on a *Mycobacterium tuberculosis* membrane vesicle or BCG membrane vesicle, wherein the first, second and third proteins have different molecular masses, and wherein detection of the presence of IgG, IgA and/or IgM directed to the first protein and the second protein and the third protein present in or on the membrane vesicle indicates active Tuberculosis disease in the subject.

A method of treating a subject with an active Tuberculosis disease is provided comprising identifying the subject as having the active Tuberculosis disease by any of the methods described herein and then administering to a subject so-identified a therapeutically effective amount of one or more anti-tuberculosis medications.

Also provided is a kit for detecting an active Tuberculosis disease in a subject comprising any one or more of the agents recited herein for detecting the one or more proteins present on a membrane vesicle as described herein, and instructions for use. In a preferred embodiment, the kit comprises at least three different agents, one each for detecting the first, second and third proteins, respectively.

DETAILED DESCRIPTION OF THE INVENTION

Figures 1A, 1B:
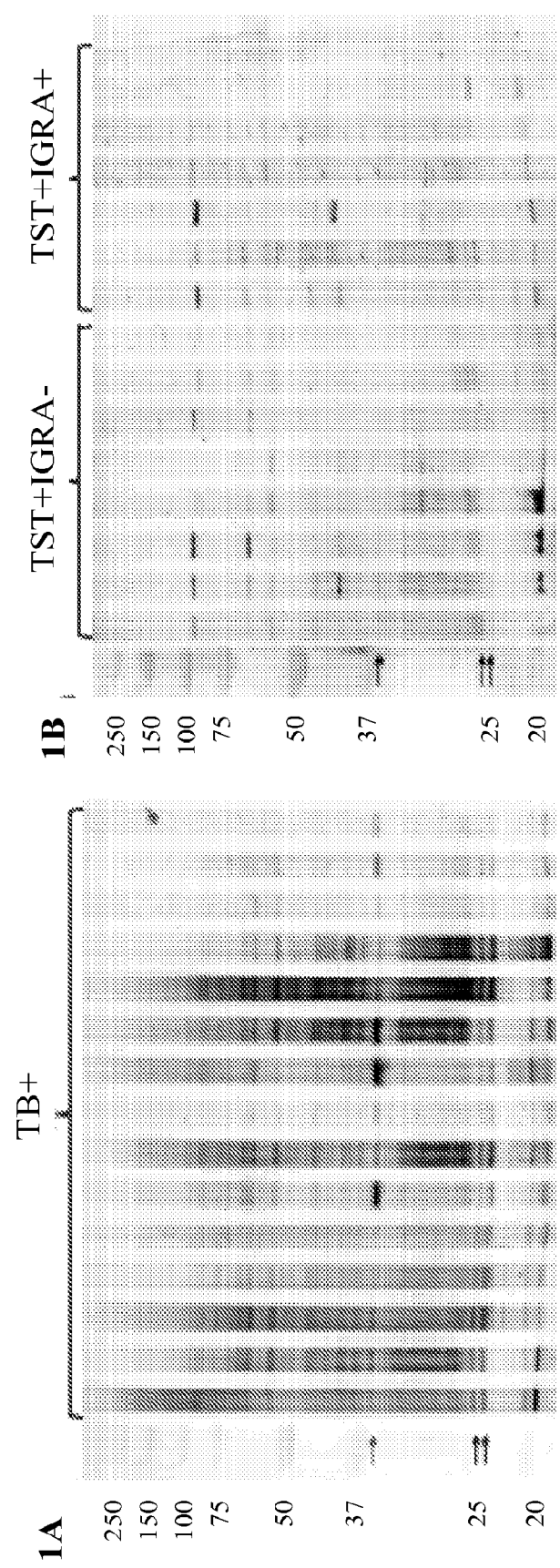
FIGS. 1A & 1B: Reactive IgG pattern to BCG MV proteins in immunoblots with A) sera from HIV− culture-proven smear-positive TB patients and B) sera from TB−/TST+ controls categorized by IGRA result. Please, note that for a sample to be considered positive, all 3 major bands need to be above the intensity cut-off determined by a receiver operating characteristics (ROC).

A method is provided of detecting active Tuberculosis disease in a subject comprising contacting a sample from the subject with a first agent capable of binding an IgG, IgA and/or IgM directed to a first protein present in or on a *Mycobacterium tuberculosis* membrane vesicle or a Bacillus Calmette-Guérin (BCG) membrane vesicle, wherein detection of the presence of IgG, IgA and/or IgM directed to the first protein present in or on the membrane vesicle indicates an active Tuberculosis disease in the subject.

In an embodiment, the sample is a serological sample.

In an embodiment, the method comprises contacting the sample from the subject with a first agent capable of binding an IgG, IgA and/or IgM directed to a first protein present in or on a *Mycobacterium tuberculosis* membrane vesicle or a BCG membrane vesicle, and with a second agent capable of binding an IgG, IgA and/or IgM antibodies directed to a second protein present in or on a *Mycobacterium tuberculosis* membrane vesicle or a BCG membrane vesicle, wherein the first and second proteins have different molecular masses, and wherein detection of the presence of IgG, IgA and/or IgM directed to the first protein and the second protein present in or on the membrane vesicle indicates active Tuberculosis disease in the subject.

In an embodiment, the method comprises contacting the sample from the subject with a first agent capable of binding an IgG, IgA and/or IgM directed to a protein present in or on a *Mycobacterium tuberculosis* membrane vesicle or on a BCG membrane vesicle, and with a second agent capable of binding an IgG, IgA and/or IgM antibodies directed to a second protein present in or on a *Mycobacterium tuberculosis* membrane vesicle or a BCG membrane vesicle, and with a third agent capable of binding an IgG, IgA and/or IgM directed to a third protein present in or on a *Mycobacterium tuberculosis* membrane vesicle or a BCG membrane vesicle, wherein the first, second and third proteins have different molecular masses, and wherein detection of the presence of IgG, IgA and/or IgM directed to the first protein and the second protein and the third protein present in or on the membrane vesicle indicates active Tuberculosis disease in the subject.

In a preferred embodiment, detection of the presence of IgG, IgA and/or IgM directed to the first protein and the second protein and the third protein present, i.e. all three, in or on the membrane vesicle indicates active Tuberculosis disease in the subject.

In an embodiment, the first, second and third proteins present in or on a *Mycobacterium tuberculosis* membrane vesicle each, independently, has a MW chosen from the group consisting of about 36 kDa, about 25 kDa, and about 23 kDa.

In an embodiment, the sample is contacted with a first agent capable of binding an IgG, IgA and/or IgM directed to a first protein present in or on the membrane vesicle having a MW of about 36 kDa, a second agent capable of binding an IgG, IgA and/or IgM directed to a second protein present in or on the membrane vesicle having a MW of about 25 kDa, and a third agent capable of binding an IgG, IgA and/or IgM directed to a third protein present in or on the membrane vesicle having a MW of about 23 kDa.

In an embodiment, at least one protein present in or on the *Mycobacterium tuberculosis* membrane vesicle or BCG membrane vesicle has a MW of about 36 kDa and is secreted antigen 85-B, serine protease PepA, protein MB3832c, secreted antigen 85-A FBPA, protein Mb0822c, protein RV0799c, antigen 85-c, Fe(III) dicitrate binding periplasmic lipoprotein, protein Mb3759, pstS1 (Rv0934), or ald (Rv2780). Rv numbers provided correspond to the Rv numbers for the H37Rv strain *M. tuberculosis* or equivalent.

In an embodiment, at least one protein present in or on the *Mycobacterium tuberculosis* membrane vesicle or BCG membrane vesicle has a MW of about 25 kDa and is protein Mb2554c, protein MPT64, lipoprotein LprA, protein RV3717, putative secreted protein, rplD, (Rv0702), rpsD (Rv3458), lipoprotein LppX (Rv2945), or lipoprotein LprG (Rv1411). In an embodiment, at least one protein present in or on the *Mycobacterium tuberculosis* membrane vesicle or BCG membrane vesicle has a MW of about 25 kDa and is protein Mb2554c, protein MPT64, lipoprotein LprA, protein RV3717, putative secreted protein, or lipoprotein LprG (Rv1411).

In an embodiment, at least one protein present in or on the *Mycobacterium tuberculosis* membrane vesicle or BCG membrane vesicle has a MW of about 23 kDa and is protein lipoprotein LpqN, 30S ribosomal protein S4, thioredoxin protein, rplD, (Rv0702), rpsD (Rv3458), HBHA (Rv0475), LprI (Rv 1541) or LppX (Rv2945). In an embodiment, at least one protein present in or on the *Mycobacterium tuberculosis* membrane vesicle or BCG membrane vesicle has a MW of about 23 kDa and is protein lipoprotein LpqN, 30S ribosomal protein S4, thioredoxin protein, HBHA (Rv0475), or LprI (Rv 1541).

In an embodiment, active Tuberculosis disease is not caused by a drug-resistant *Mycobacterium tuberculosis* infection.

In an embodiment, the method further comprises obtaining the sample from the subject prior to contacting the sample with the agent(s).

In an embodiment, the method further comprises administering to a subject found to have active Tuberculosis disease by the method, a therapeutically effective amount of one or more anti-tuberculosis medications.

In an embodiment, the first, second and/or third agent is an anti-idiotype isolated antibody, or an anti-idiotype antigen-binding fragment thereof directed against an antigen-binding site of the IgG, IgA or IgM.

In an embodiment, the first, second and/or third agent is an isolated protein, a protein having the same sequence of which isolated protein is present in or on a *Mycobacterium tuberculosis* membrane vesicle or BCG membrane vesicle, wherein the protein has a MW of about 36 kDa, about 25 kDa or about 23 kDa.

In an embodiment, the first agent comprises an isolated protein that is secreted antigen 85-B, serine protease PepA, protein MB3832c, secreted antigen 85-A FBPA, protein Mb0822c, protein RV0799c, antigen 85-c, Fe(III) dicitrate binding periplasmic lipoprotein, protein Mb3759, pstS1 (Rv0934), or ald (Rv2780).

In an embodiment, the second agent comprises an isolated protein that is protein Mb2554c, protein MPT64, lipoprotein LprA, protein RV3717, putative secreted protein, rplD, (Rv0702), rpsD (Rv3458), lipoprotein LppX (Rv2945), lipoprotein LprG (Rv1411). In an embodiment, the second agent comprises an isolated protein that is protein Mb2554c, protein MPT64, lipoprotein LprA, protein RV3717, putative secreted protein, or lipoprotein LprG (Rv1411).

In an embodiment, the third agent comprises an isolated protein that is protein lipoprotein LpqN, 30S ribosomal protein S4, thioredoxin protein, rplD, (Rv0702), rpsD (Rv3458), HBHA (Rv0475), LprI (Rv 1541) or LppX (Rv2945). In an embodiment, the third agent comprises an isolated protein that is protein lipoprotein LpqN, 30S ribosomal protein S4, thioredoxin protein, HBHA (Rv0475), or LprI (Rv 1541).

In an embodiment, the first, second and/or third agent is an isolated peptide. In an embodiment, the first, second and/or third agent is an isolated peptide having a sequence identical to a portion of protein is present in or on a *Mycobacterium tuberculosis* membrane vesicle or BCG membrane vesicle, wherein the protein has a MW of about 36 kDa, about 25 kDa or about 23 kDa. In an embodiment, the first, second and/or third agent is an isolated peptide having a sequence identical to a portion of one of the proteins listed hereinabove. In an embodiment, the first, second and/or third agent is an isolated mimotope having a sequence similar to or identical to an epitope of one of the IgG, IgA and/or IgM described hereinabove.

In an embodiment, the sample comprises serum, plasma or whole blood. In an embodiment, the sample comprises a bodily fluid. Non-limiting examples of bodily fluids include pleural fluid, saliva and cerebro-spinal fluid.

In an embodiment, the method further comprises obtaining the sample from the subject prior to contacting the sample with the agent(s).

In an embodiment, the first, second and/or third agent is an anti-idiotype isolated antibody, or an anti-idiotype antigen-binding fragment thereof directed against an antigen-binding site of the IgG, IgA or IgM.

In an embodiment, the agent or agents are each detectably labeled.

In an embodiment, the IgG, IgA or IgM is determined to be present by detection of binding the agent or agent(s) to the IgG, IgA or IgM.

In an embodiment, the IgG, IgA or IgM is determined to be present by detection of one or more detectable label(s) of the agent or agent(s) bound to the IgG, IgA or IgM.

In an embodiment, the subject is a mammal. In a preferred embodiment, the subject is a human.

In an embodiment, the one or more proteins are present in or on a *Mycobacterium tuberculosis* membrane vesicle.

In an embodiment, the one or more proteins are present in or on a BCG membrane vesicle.

A method of treating a subject with an active Tuberculosis disease is provided comprising identifying the subject as having the active Tuberculosis disease by any of the methods described herein and then administering to a subject so-identified a therapeutically effective amount of one or more anti-tuberculosis medications.

Also provided is a method of detecting active Tuberculosis disease in a subject comprising contacting a sample from the subject, wherein the sample has been treated so as to permit detection of the subject's antibodies to one or more proteins on a *Mycobacterium tuberculosis* membrane vesicle or *Bacillus* Calmette-Guérin (BCG) membrane vesicle, with a first agent capable of binding an IgG, IgA and/or IgM directed to a protein present in or on a *Mycobacterium tuberculosis* membrane vesicle or BCG membrane vesicle, and with a second agent capable of binding an IgG, IgA and/or IgM antibodies directed to a second protein present in or on a *Mycobacterium tuberculosis* membrane vesicle or BCG membrane vesicle, and with a third agent capable of binding an IgG, IgA and/or IgM directed to a third protein present in or on a *Mycobacterium tuberculosis* membrane vesicle or BCG membrane vesicle, wherein the first, second and third proteins have different molecular masses, and wherein detection of the presence of IgG, IgA and/or IgM directed to the first protein and the second protein and the third protein present in or on the membrane vesicle indicates active Tuberculosis disease in the subject.

In an embodiment, the first, second and third proteins present in or on a *Mycobacterium tuberculosis* membrane vesicle or BCG membrane vesicle each, independently, has a MW chosen from the group consisting of about 36 kDa, about 25 kDa, and about 23 kDa.

In an embodiment, the sample is contacted with a first agent capable of binding an IgG, IgA and/or IgM directed to a first protein present in or on a *Mycobacterium tuberculosis* membrane vesicle or BCG membrane vesicle having a MW of about 36 kDa, a second agent capable of binding an IgG, IgA and/or IgM directed to a second protein present in or on a *Mycobacterium tuberculosis* membrane vesicle or BCG membrane vesicle having a MW of about 25 kDa, and a third agent capable of binding an IgG, IgA and/or IgM directed to a third protein present in or on a *Mycobacterium tuberculosis* membrane vesicle or BCG membrane vesicle having a MW of about 23 kDa.

In an embodiment, the at least one protein present in or on the membrane vesicle has a MW of about 36 kDa and is secreted antigen 85-B, serine protease PepA, protein MB3832c, secreted antigen 85-A FBPA, protein Mb0822c, protein RV0799c, antigen 85-c, Fe(III) dicitrate binding periplasmic lipoprotein, protein Mb3759, pstS1 (Rv0934), or ald (Rv2780).

In an embodiment, the at least one protein present in or on the membrane vesicle has a MW of about 25 kDa and is protein Mb2554c, protein MPT64, lipoprotein LprA, protein RV3717, putative secreted protein, rplD, (Rv0702), rpsD (Rv3458), lipoprotein LppX (Rv2945), lipoprotein LprG (Rv1411). In an embodiment, the at least one protein present in or on the membrane vesicle has a MW of about 25 kDa and is protein Mb2554c, protein MPT64, lipoprotein LprA, protein RV3717, putative secreted protein, or lipoprotein LprG (Rv1411).

In an embodiment, the at least one protein present in or on the *Mycobacterium tuberculosis* membrane vesicle has a MW of about 23 kDa and is protein lipoprotein LpqN, 30S ribosomal protein S4, thioredoxin protein, rplD, (Rv0702), rpsD (Rv3458), HBHA (Rv0475), LprI (Rv 1541) or LppX (Rv2945). In an embodiment, the at least one protein present in or on the *Mycobacterium tuberculosis* membrane vesicle has a MW of about 23 kDa and is protein lipoprotein LpqN, 30S ribosomal protein S4, thioredoxin protein, HBHA (Rv0475), or LprI (Rv 1541).

In an embodiment, the subject is a human.

In an embodiment, the one or more proteins are present in or on a *Mycobacterium tuberculosis* membrane vesicle.

In an embodiment, the one or more proteins are present in or on a BCG membrane vesicle.

Also provided is a kit for detecting an active Tuberculosis disease in a subject comprising any one or more of the agents recited herein for detecting the one or more proteins present on a membrane vesicle as described herein, and instructions for use. In a preferred embodiment, the kit comprises at least three different agents, one each for detecting the first, second and third proteins, respectively.

In an embodiment, the kit further comprises a sample collecting receptacle and/or reagents for the method.

As used herein, "about" with regard to 23 KDa, 25 KDa or 36 KDa molecular weight encompasses the molecular weight stated and all tenths of an integer of the stated molecular mass either side to ±2 kDa. For example, "about 25 kDa" encompasses 23.0, 23.1, 23.2, 23.3, 23.4, 23.5, 23.6, 23.7, 23.8, 23.9, 24, 24.1, 24.2, 24.3, 24.4, 24.5, 24.6, 24.7, 24.8, 24.9, 25, 25.1, 25.2, 25.3, 25.4, 25.5, 25.6, 25.7, 25.8, 25.9, 26, 26.1, 26.2, 26.3, 26.4, 26.5, 26.6, 26.7, 26.8, 26.9, 27 kDa. In an embodiment, the "about" with regard to 23 KDa or 25 KDa only encompasses the molecular weight stated and all tenths of an integer of the stated molecular weight either side to ±1 kDa. In an embodiment, the about 23 KDa protein is of lower molecular weight than the about 25 KDa protein. Each molecular weight within the stated range of "about" to the tenght of an integer are also individually embodied.

Anti-tuberculosis medications are well-known in the art and include cycloserine (Seromycin), ethambutol (Myambutol), ethionamide (TrecatorSC), isoniazid (Nydrazid, Laniazid), pyrazinamide, rifabutin (Mycobutin), and rifampin (Rifadin, Rimactane).

In a preferred embodiment, the *mycobacterium* membrane vesicles are from an H37Rv strain *M. tuberculosis*.

In an embodiment of the inventions described herein, the vesicles are from a *Mycobacterium tuberculosis*, and the *Mycobacterium tuberculosis* is one of the following: *Mycobacterium tuberculosis* H37Rv, BTB05-552, BTB05-559, CDC1551, CTRI-2, F11, H37, H37Ra, HN878, KZN 1435, KZN 4207, KZN R506, KZN V2475, R1207, RGTB327, S96-129, X122, '98-R604 INH-RIF-EM', 02_1987, 210, 94_M4241A, C, CDC1551A, CPHL_A, CTRI-4, EAS054, GM 1503, K85, KZN 605, OSDD071, OSDD504, OSDD518, SUMu001, SUMu002, SUMu003, SUMu004, SUMu005, SUMu006, SUMu007, SUMu008, SUMu009, SUMu010, SUMu011, SUMu012, T17, T46, T85, T92, W-148, str. Haarlem, 210_16C10, 210_16C2_24C1, 210_16C2_24C2, 210_32C4, 210_4C15, 210_4C15_16C1, 210_4C15_16C1_48C1, 210_4C15_16C1_48C2, 210_4C15_16C1_56C1, 210_4C15_16C1_56C2, 210_4C31, 210_4C31_16C1, 210_4C31_16C1_24C1, 210_4C31_16C1_40C1, 210_4C31_16C2, 210_8C1, 210_8C6, BC, CTRI-3, H37Rv_2009, NJT210GTG, str. Erdman=ATCC 35801, str. Erdman WHO, CCDC5079, CCDC5180, RGTB423, UT205, CTRI-1, H37RvAE, H37RvCO, H37RvHA, H37RvJO, H37RvLP, H37RvMA, LAM7, NCGM2209, RGTB306, WX1, WX3, XDR1219, XDR1221, str. Beijing/W BT1, or str. Erdman (ATCC 35801). For H37Rv genome, see NCBI Reference Sequence: NC_000962.2, see GenBank: AL123456.2.

In an embodiment of each of the methods described herein, the method further comprises treating a subject identified by the method as having active Tuberculosis disease with an anti-tuberculosis medication. In an embodiment, a first line, second line or third line anti-tuberculosis medication is used. In an embodiment, the anti-tuberculosis medication comprises one or more of isoniazid, rifampicin, pyrazinamide, and ethambutol. In an embodiment, the anti-tuberculosis medication comprises one or more of an aminoglycoside, capreomycin, viomycin, enviomycin, a fluoroquinolones, athioamide, a cycloserine or terizidone.

The methods disclosed herein involving subjects can be used with any species capable of being infected by *M. tuberculosis*. In a preferred embodiment, the subject is a mammalian subject or an avian subject. Most preferably, the subject is mammalian and is a human.

All combinations of the various elements described herein are within the scope of the invention unless otherwise indicated herein or otherwise clearly contradicted by context. Every combination in each of the methods, compositions and assays herein of a choice of any one of the about 36 KDa proteins as listed herein, with a choice of any one of the about 25 KDa proteins as listed herein, and with a choice of any one of the about 23 KDa proteins as listed herein, i.e. a combination of three different proteins, are each individually encompassed by the invention.

This invention will be better understood from the Experimental Details, which follow. However, one skilled in the art will readily appreciate that the specific methods and results discussed are merely illustrative of the invention as described more fully in the claims.

Experimental Details

Introduction

Herein are disclosed novel results showing that Ab responses to proteins enriched in (MVs) of pathogenic mycobacteria constitute a TB biomarker signature that has tremendous diagnostic information. MVs differ significantly from exosomes in that MVs are directly released by bacteria, while exosomes are secreted by (infected) mammalian cells.

MVs provide an effective way for intracellular bacteria to release concentrated immune-modulatory factors into the host. Evaluating the host immune response to MVs provides a unique opportunity for identification of novel biomarkers. No prior study has characterized the immune responses to mycobacterial MVs with the goal of identifying a TB Ab biomarker signature. A novelty of the present approach includes the signature pattern revealed.

The identification of easily detectable biomarkers for active tuberculosis (TB) is a global health priority [1]. Serum antibodies (Abs) can be detected by "dip-stick" formats that provide extremely rapid results [2-4]. However, TB serology has suffered from decades of unsuccessful attempts to develop accurate tests for TB [5-7]. The results herein show that Ab responses to a protein signature enriched in membrane vesicles (MVs) of pathogenic mycobacteria constitute a robust TB biomarker, permitting a simple, rapid MV protein-based diagnostic test for TB.

MVs have largely been studied in Gram negative bacteria where they facilitate the transport of virulence factors into the host [8, 9]. It has recently been demonstrated that *Mycobacterium tuberculosis* (Mtb) and *Mycobacterium bovis Bacillus* Calmette-Guérin (BCG) also produce MVs (FIG. 1) that contribute to mycobacterial virulence in mice [10]. MVs provide an effective way for intracellular bacteria to release immune-modulatory factors and the host immune responses to MVs provide a unique opportunity for identification of novel biomarkers. Thus far, the immunogenicity of mycobacterial MVs has not been studied in humans.

Herein, a reactive pattern has been characterized in BCG and Mtb MV immunoblots that is present in sera from U.S. HIV uninfected (i.e. HIV–) TB patients, but absent in TST positive BCG vaccinated healthy volunteers. Specifically, bands at ~36, ~25, and ~23 kDa were simultaneously recognized by serum IgG from 15/15 sputum smear-positive TB patients, but 0/15 TST+ controls, of which 8/15 had a negative and 7/15 a positive interferon-gamma release assay (IGRA) result indicative of latent Mtb infection (LTBI). This Ab response to specific mycobacterial MV proteins is strongly and significantly associated with disease, but not with LTBI or exposure to other mycobacteria, thus providing a highly sensitive and specific TB biomarker signature.

Identifying a reactive pattern to several antigens has been more accurate than other Ab-detection methods (e.g. ELISA) for a variety of difficult to diagnose infectious diseases.

Function and relevance of MVs: Vesicles have largely been studied in Gram negative and, lately, also in Gram positive bacteria where their release facilitates the transportation of a virulence factors into the host [8, 9].

Immunogenicity of MVs was previously demonstrated for several organisms such as *N. meningitides, S. typhimurium, V. cholera* and *B. anthraces* by immunization studies [32-41]. Ab responses elicited in these vaccine studies were predominantly IgG [34, 38], with some murine studies also reporting IgA and IgM [35, 37]. Mycobacterial MVs (see [10]) can vary between 60 to 300 nm in diameter (FIG. 1) and their composition includes phospholipids, polysaccharides, and a large number of lipoproteins. The administration of MVs from Mtb and BCG to mice prior to pulmonary Mtb infection resulted in an enhanced local inflammatory response with increased bacterial replication in lungs and spleen. Hence, MVs from pathogenic mycobacteria appear to be a delivery mechanism for immunologically active molecules that contribute to mycobacterial virulence.

An overview of a non-limiting methodology for identifying a suitable antigen signature is the following:

a) separate MV proteins by two-dimensional (2D) gel electrophoresis and immunoblot against TB+ sera;
b) perform mass spectrometric protein identification of reactive gel spots at sizes of major bands;
c) generate vectors and express (in vitro) MV proteins identified by mass spectrometry;
d) optimize immunoblots with recombinant purified proteins; and
e) verify Ab responses to recombinant proteins in TB and ORD patients.

Figures 2A, 2B, 2C:
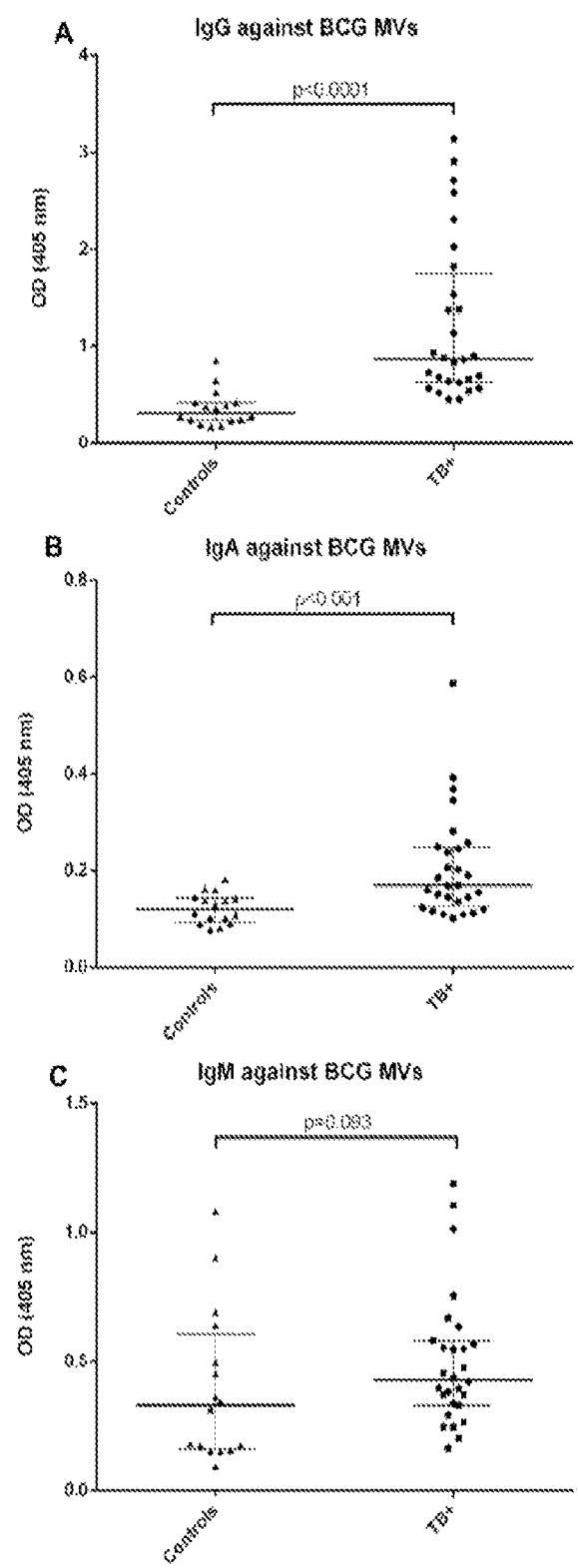
FIG. 2A-2C: Antibody isotype responses against BCG MVs in TB patients and TST þ controls. A. IgG responses against BCG MVs; B. IgA responses against BCG MVs; C. IgM responses against BCG MVs. Statistical analysis with Mann-Whitney U test. Bars show median values with interquartile range.
Figures 3A, 3B:
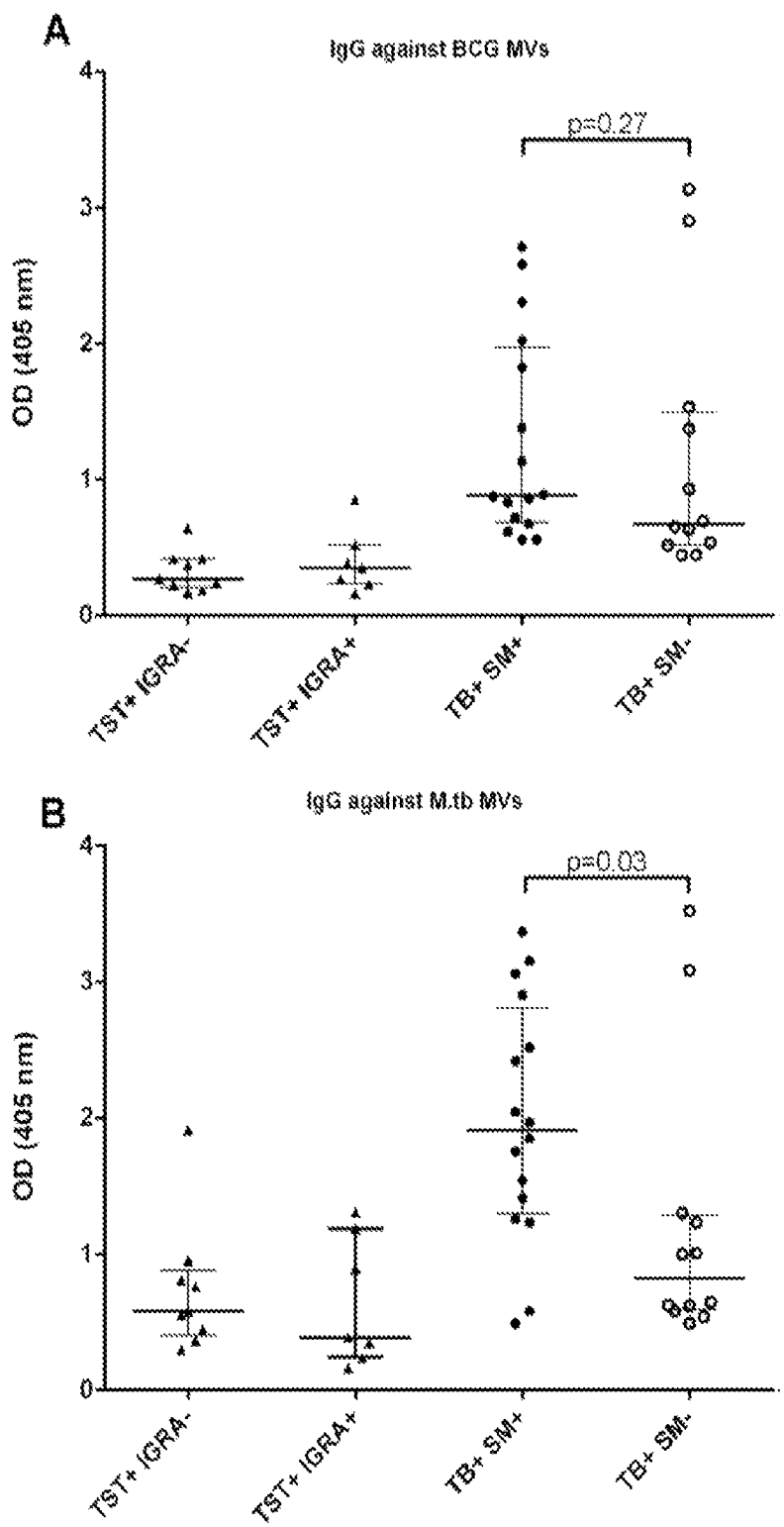
FIG. 3A-3B: IgG responses to BCG (A) and *M. tuberculosis* MVs (B), demonstrating significantly higher IgG titers in smear-positive compared to smear-negative TB patients against *M. tuberculosis* MVs but not against BCG MVs. Statistical analysis with Mann-Whitney U test. Bars show median values with interquartile range.
Figures 4A, 4B:
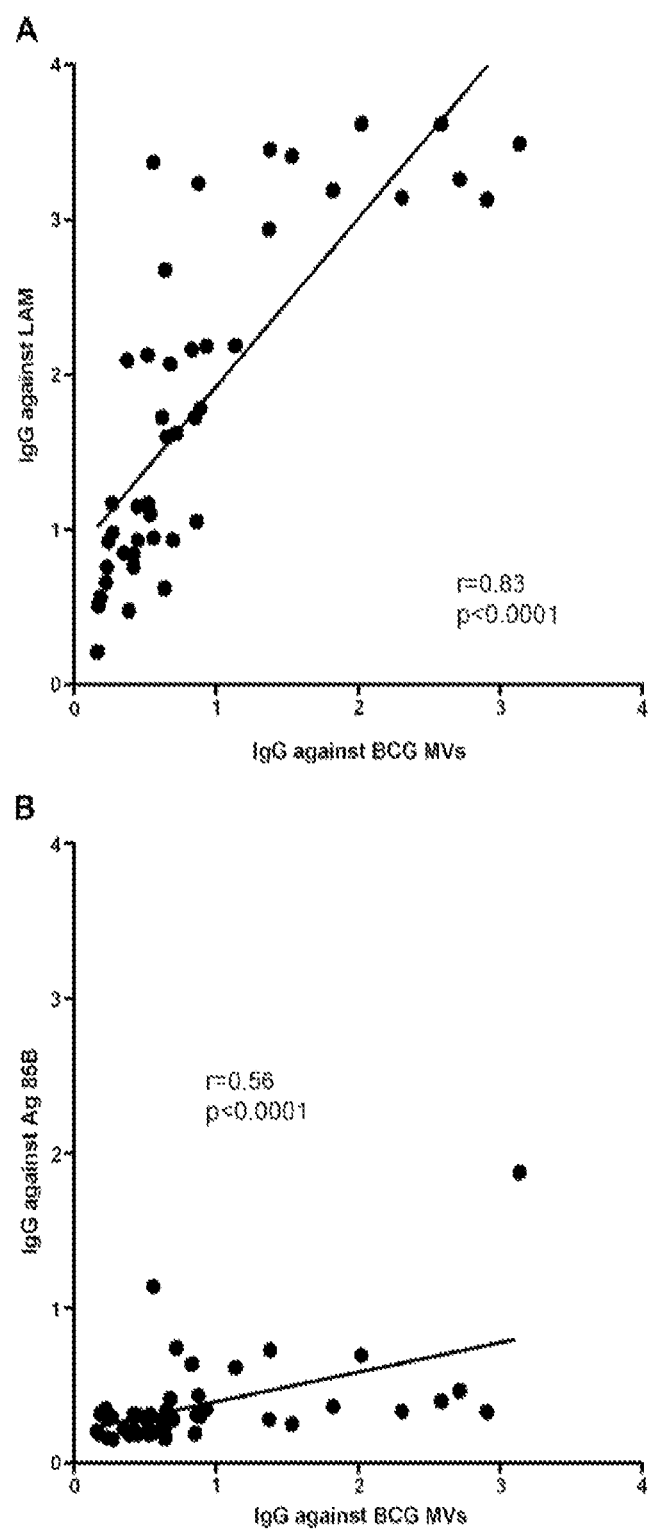
FIG. 4A-4B: Correlations of IgG responses between A. BCG MVs and cell wall glycolipid lipoarabinomannan (LAM), and B. BCG MVs and protein antigen Ag 85B. Statistical analysis with Spearman rank correlation test.
Figures 5A, 5B, 5C, 5D:
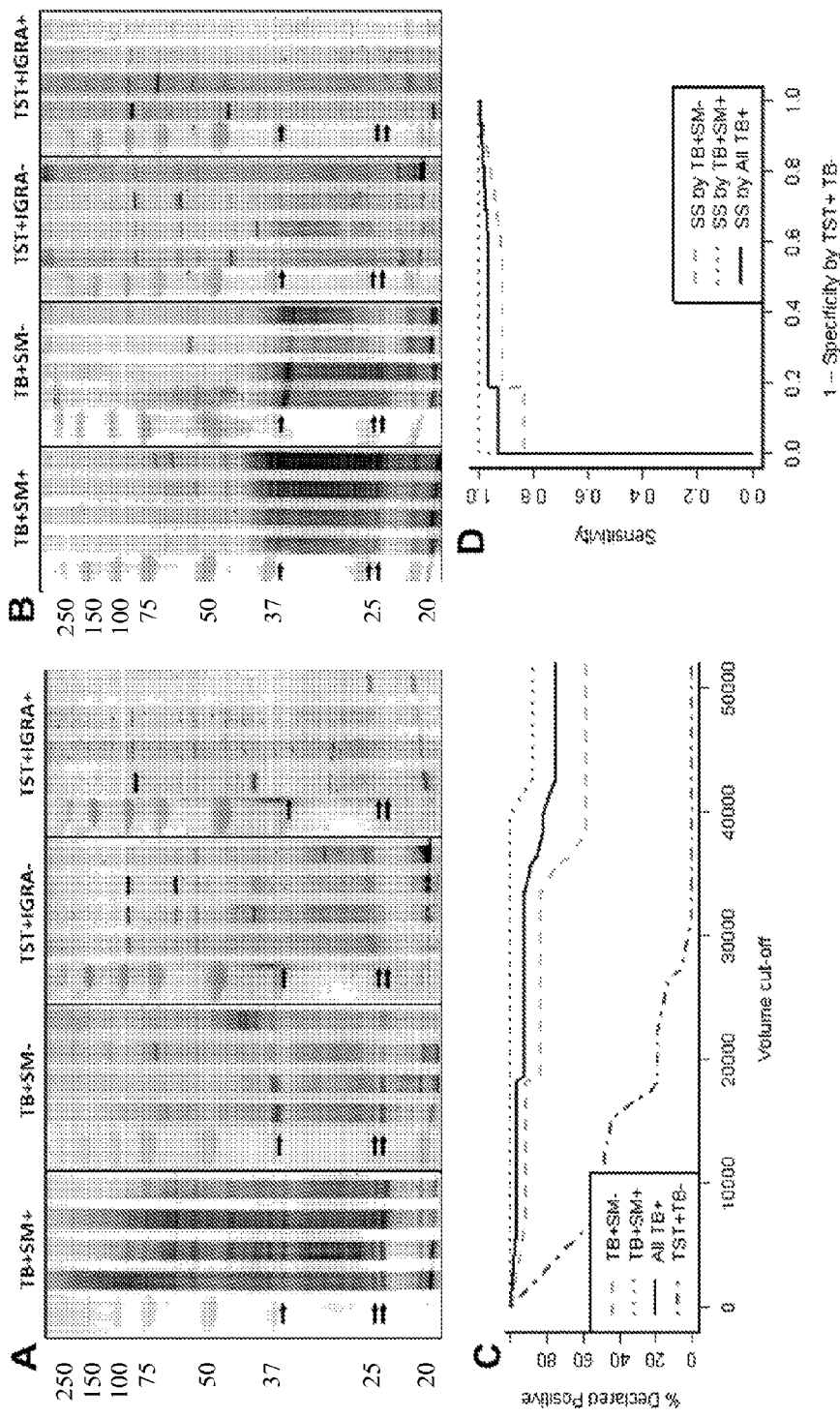
FIG. 5A-5D: AeB. Reactive IgG pattern to BCG MV (A) and *M. tuberculosis* MV (B) proteins in immunoblots with 4 representative sera from smear-positive and smear-negative TB patients and from TST+ TB− BCG vaccinated controls categorized by interferon-gamma release assay (IGRA) result demonstrating 3 bands w36, 25 and 23 kDa that are simultaneously
recognized with sera of TB+ cases but not BCG vaccinated TST+ controls without or with latent *M. tuberculosis* infection (LTBI). Due to higher background with *M. tuberculosis* MV immunoblots, BCG MV immunoblots were used for further analysis; C. Proportion of positive immunoblots (y-axis) for smear-positive, smear-negative, and all TB+ cases as well as TST+ controls according to band intensity in pixel$^3$ (volume; x-axis) indicating that optimal cut-off values can range between about 30,000 and 35,000 pixel$^3$; and D. Receiver-operating characteristics (ROC) curve for optimal cut-off at 30,000 pixel$^3$.
Figure 6:
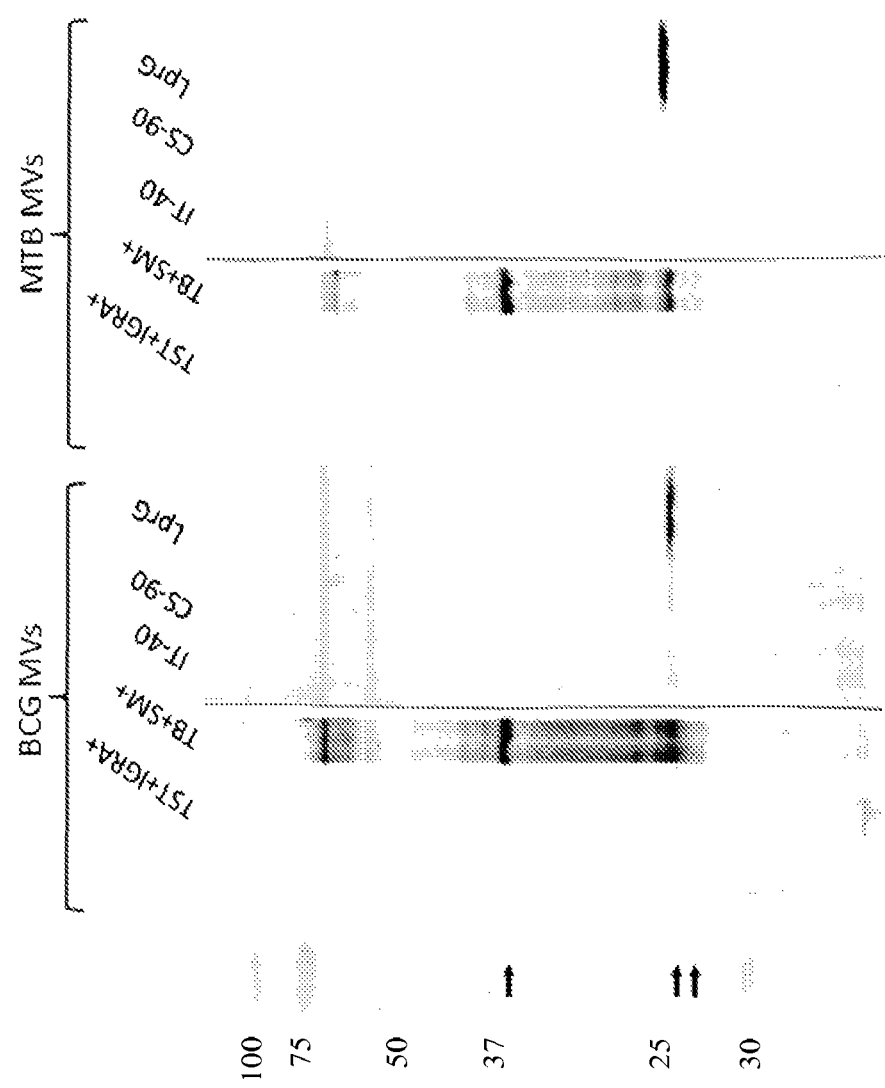
FIG. 6: BCG and *M. tuberculosis* MV immunoblots probed with sera from a TST þ IGRA þ control and smear-positive TB patients, and mAbs against the Ag 85 complex (IT-40 and CS-90) and the lipoprotein LprG. The mAb against LprG is reactive, while no reactivity is observed with mAbs against Ag 85.

Immunogenicity studies with mycobacterial MV show a reactive IgG pattern in BCG and Mtb Western blot profiles that is present in sera from U.S. HIV– TB patients, but absent in TST+ BCG vaccinated healthy volunteers. Visual and quantitative analysis of band intensity with the program Image Quant (GE Healthcare, PA) identified three bands at ~36, 25, and 23 kDa that were simultaneously recognized by serum IgG from 15/15 sputum smear-positive TB patients but 0/15 TST+ controls of which 8/15 had a negative and 7/15 a positive IGRA result indicative of LTBI (FIGS. 2&3). Optimal cutoff for intensity of all bands was determined by receiver-operating characteristics (ROC; FIG. 4).

About 50-60 Mtb and BCG MV-associated proteins have previously been identified (e.g., see [10]). About 20 of these proteins have a molecular mass (kDa) that corresponds to that of the major immunoblot bands seen (Table 1). Since it is possible to screen for Ab responses to the entire Mtb proteome, the proteins previously associated with TB and within the kDa range of our main reactivity bands have been reviewed [5, 7, 28, 42] (Table 1).

Of note is also the homogeneity of IgG responses to MV proteins demonstrated by the simultaneous recognition of 3 immunoblot bands. This is in contrast to the heterogeneity of Ab responses in HIV– TB patients to other antigens evaluated for TB serodiagnosis [28, 30, 43, 44], suggesting that mycobacterial MVs are highly immunogenic. Given that a comparable serological specificity can be achieved with both Mtb and BCG vesicles, it is believed that the Ab signature is in response to sufficient Mtb burden releasing MVs and causing disease because it is absent in controls with a history of exposure to other mycobacteria (e.g. BCG vaccination) or with LTBI. Significantly, the method is able to distinguish active tuberculosis disease from simple MTb infection.

TABLE 1

MV-associated proteins

| Mtb/BCG MV protein | Molecular Mass (kDa) | Previously Associated with TB |
|---|---|---|
| Hypothetical protein Mb3759 | 37.4 | |
| FEIII-dicitrate-binding periplasmic lipoprotein | 37.1 | |
| Antigen 85-C | 36.8 | X |
| Hypothetical protein RVO799c | 36.1 | |
| Hypothetical protein Mb0822c | 35.9 | |
| Secreted antigen 85-A FBPA | 35.8 | X |
| Hypothetical protein MB3832c | 35.3 | |
| Serine Protease PepA | 34.9 | |
| Secreted antigen 85-B | 34.4 | X |
| Hypothetical protein MB2554c | 25.1 | |
| Protein MPT64 | 25.1 | X |
| Lipoprotein LprA | 25.0 | |
| Hypothetical protein RV3717 | 24.9 | |
| Putative secreted protein | 24.7 | |
| Lipoprotein LprG | 24.6 | X |
| Hypothetical Protein Rv3036c | 24.6 | |
| Lipoprotein LppX | 24.3 | |
| Lipoprotein LpqN | 23.7 | |

TABLE 1-continued

MV-associated proteins

| Mtb/BCG MV protein | Molecular Mass (kDa) | Previously Associated with TB |
|---|---|---|
| 30S ribosomal protein S4 | 23.3 | |
| Thioredoxin protein | 23.0 | |

Other proteins within the ranges are:
pstS1 or 38 kDa protein, also called phoS1 or phoS (Rv0934) - about 36 kDa;
ald, 38.7 kDa (Rv2780) - about 36 kDa;
LprG, 24.5 kDa MW (Rv1411) - about 25 kDa;
LppX, 24.1 kDa MW (Rv2945) - about 25 kDa;
rplD, 23.7 kDa (Rv0702) - about 23 kDa;
rpsD, 23.4 kDa (Rv3458) - about 23 kDa;
HBHA 21.5 kDa (Rv0475) - about 23 kDa; and
LprI, 22 kDa (Rv 1541) - about 23 kDa.

Materials and Methods

Subjects: Samples are categorized into TB (n=50; sputum smear-negative (n=25) and smear-positive (n=25)) and ORD (n=50; Table 2). Sera are obtained under an IRB-approved protocol and are stored at −80° C. Inclusion criteria are age ≥21 years and receipt of sputum smears for AFB and mycobacterial cultures. Exclusion criteria are receipt of anti-tuberculosis treatment for >2 weeks or within the year prior to enrollment. Written informed consent is obtained from all subjects prior to enrollment. TB cases are confirmed by the gold standard test for TB diagnosis—a respiratory specimen culture positive for Mtb. Sputum smears are considered positive if one of the initial 3 smears was positive for AFB. Subjects are categorized as ORD if they have a respiratory culture negative for Mtb, and an ORD diagnosis as per physician's discharge note. Diagnosis of NTM lung disease is based on criteria according to the American Thoracic Society [47].

TABLE 2

Anticipated diagnosis of ORD patients {n = 50}

| Bacterial pneumonia | Bronchitis | NTM disease | Lung Abscess | Lung cancer |
|---|---|---|---|---|
| n = 28 (56%) | n = 10 {20%} | n = 3 {6%} | n = 6 {12%} | N = 3 {6%} |

Mycobacterial cultures and MV isolation & purification: BCG and Mtb MVs are harvested at 3 different culture lengths and compared for immunogenicity with previously Ab signature positive TB sera (n=6) and Ab signature negative TST+ controls (n=6). Production of MVs is standardized to the conditions that result in MVs constituting the most accurate TB Ab signature. Where no significant differences in Ab signature is observed between Mtb and BCG MVs, BCG MVs can be used for immunoblotting.

Mycobacterial cultures: Mycobacterial pre-cultures and cultures are performed as described [10]. Briefly, 10 ml of 7H9 Media+0.05 tyloxapol is inoculated with a glycerol stock of *M. bovis* BCG (Pasteur) or Mtb (H37Rv) and grow at 37° C. until stationary phase (7-10 d; determined by optimal OD of about 1±0.2 at 540 nm). A 1 ml volume of the stationary phase pre-cultures is then incubated in 500 ml minimal media with no tyloxapol in 2 L capacity roller bottles and cultured for 8-12 d at 37° C.

Mycobacterial MV isolation & purification: Vesicles are harvested after 8, 10 and 12 d to determine optimal culture time for MV production. These time intervals are chosen based on ~18 h of doubling time for BCG and Mtb, and a personal observation that sufficiently detectable vesicle production requires at least 8 d of culture.

MV isolation and purification involves a series of centrifugation and density gradient purification steps [10, 36]. Briefly, cells from 500 ml cultures are collected by centrifugation (3,450 g for 15 minutes, 4° C.) and the supernatants are filtered through a 0.45 µm polyvinylidene difluoride membraner (Millipore, MA). Next, the filtered supernatant is concentrated with an Amicon Ultrafiltration System (Millipore, MA) using a 100-kDa exclusion filter. The concentrate is then centrifuged at 60,000 rpm for 1 h at 4° C. to sediment the vesicular fraction into a pellet. The pellet is resuspended in 1 ml of PBS and stored at −20° C. The protein concentration of the vesicle preparation will be measured using a BCA Protein Assay Kit as per manufacturer's instructions (Thermo Scientific, IL).

Immunoblotting: Ab reactivity to mycobacterial MVs proteins is determined by Western blot. A 50 µg MV solution is electrophoresed in stacking and 12% SDS acrylamide resolving 2D prep gels as described [48]. Electrophoresis is performed in the Bio-Rad Mini-Protean II system at 100 V initially followed by 140 V, until the protein front reaches the bottom of the gel. The gel proteins are transferred to nitrocellulose membranes via the Invitrogen iBlot® Dry Blotting System (Life Technologies, NY). Following transfer, membranes are blocked for 1 h at RT using 5% milk in TBS+0.01% Tween 20. Serum samples, diluted 1:100 in blocking solution, will be incubated at 4° C. over night using the multi-channel blotting system Surf-Blot 7.5 (Idea Scientific, MN). This system allows for analysis of up to 16 samples on one membrane with the advantage of small sample volume requirements. Next, the membrane is washed with PBS+0.01% Tween 20 and incubated for 45 min at RT with alkaline phosphatase (AP)-labeled goat anti-human IgG, IgA or IgM (Sigma-Aldrich, MO) diluted 1:1000 in PBS+0.01% Tween 20. Bands are visualized using the AP substrate SIGMAFAST BCIP®/NBT (Sigma-Aldrich, MO). Images of the Western membranes are acquired via the Epson Expression 10000XL high resolution scanner (Epson, CA). Band intensity will be analyzed by densitometry using ImageQuant TL, Version 7.0 (GE Healthcare, PA) [49, 50]. Backgrounds are determined for each lane individually and set as a straight line at the lowest point of the histological profile of the lane. Bands are considered positive if the band volume (pixel$^3$), representing the bands signal intensity as well as thickness, is greater than the cut-off determined by ROC curve analysis (e.g. 30,000 pixel$^3$).

Statistical analysis: Samples are evaluated from TB cases (n=50) and ORD (n=50) controls to determine IgG, IgA and IgM responses to MVs (Table 3). To make cases representative of the reported sensitivity (i.e. 50%) for sputum microscopy [19, 21], the TB group is comprised of 25 sputum AFB smear positive and 25 smear-negative TB cases. Similarly, the ORD patient set includes 3 AFB smear positive patients with NTM. Based on our preliminary immunoblot results, at least 3 main bands are recognized by serum IgG from TB but not ORD patients. Bands are considered positive if the band volume intensity (pixel$^3$) is greater than the cut-off determined by ROC curve analysis in preliminary studies (30,000 pixel$^3$). Assay results are considered positive if 3/3 bands are positive and negative if 2/3 or less bands are positive. Sensitivity and specificity of IgG responses to MV proteins are computed based on the gold standard test of a positive culture for Mtb. Exact one-sided binomial test [51] is performed to test the sensitivity of the method among HIV− TB cases and the specificity among HIV− ORD controls are simultaneously greater than 0.50 and 0.80, respectively, using a family-wise type I error rate of 5%. This means the lower-bounds of the 95% (joint confidence level) exact confidence intervals of sensitivity and specificity are compared to these numbers.

TABLE 3

| HIV-TB suspects | | | |
|---|---|---|---|
| | TB | ORD | Total |
| Smear+ | 25 | 3 | 28 |
| Smear− | 25 | 47 | 72 |
| Total | 50 | 50 | 100 |

MV proteins are separated by two-dimensional (2D) gel electrophoresis, plot against pooled sera from HIV− TB patients, and mass spectrometric protein identification of reactive gel spots performed at the mass of the main reactivity bands determined in immunoblots. Identified proteins are expressed in vitro, e.g. using plasmids, and purified. After optimizing immunoblots, Ab responses can be verified to recombinant proteins with sera from TB and ORD patients. The proteins extracted from MVs are re-suspended in 2D electrophoresis sample buffer (7M urea, 2M thiourea, 4% CHAPS, 40 mM DTT), added with Destreak reagent (GE Life Sciences, PA) diluted to 0.5% with IPG Buffer pH 3-10NL. The solution is divided into 2 portions containing 160 μg and 230 μg of MV proteins for 2D electrophoresis. The smaller portion is used for Western blotting to identify spots of interest based on Ab reactivity in pooled samples from 5 HIV− smear-positive TB patients with strong reactivity to major MV protein bands in preliminary immunoblots. The second portion is utilized in a Coomassie Blue stained gel for protein excision and identification by mass spectrometry. The proteins are initially separated by pI on a 13 cm IPG strip pH3-10NL for a total of 20 kVh. After reduction and alkylation using DDT and iodoacetamide, the proteins are separated by molecular mass using 10% acrylamide SDSPAGE. Based on Western blot results the proteins are picked from the Coomassie-stained gel and digested with trypsin in 25 mM ammonium bicarbonate/ 0.01% ProteaseMax (Promega, WI) at 50° C. for 1 h. The resulting digest is cleaned with C18 ZipTip (Millipore, MA) and the peptides eluted onto a matrix-assisted laser desorption/ionization (MALDI) plate with a saturated solution of α-cyanohydroxycinnamic acid in 70% acetonitrile/0.1% trifluoroacetic acid. MS/MS analysis of the digested samples is carried out using the Applied Biosystems/AB Sciex 4800 MALDI-TOF/TOF (ABSciex, MA) operated at 20 kV accelerating voltage in the reflector positive ion mode as described [58]. The MS/MS data generated are converted to mgf files and searched against the Mtb database (e.g. see www.broad.mit.edu).

Briefly, recombinant bacterial expression plasmids, encoding C-terminal hexahistidine fusions of the MV proteins, can be expressed in E. coli and purified with the final Ni-affinity chromatographic steps implemented on an AktaFPLC system (GE Healthcare, PA) equipped with 1 ml HisTrapHP (GE Healthcare Li, PA) columns followed by cleavage of His tag. Immunoblotting can be basically performed as described above with the difference that Ab reactivity to recombinant proteins instead of whole MVs is tested. Immunoblots can be optimized by loading various protein concentrations ranging from 50-100 μg/gel into SDS gels to determine optimal protein loading while keeping the serum dilution of 1:100 constant. Then Ab responses can be verified to recombinant proteins with TB and ORD sera.

Statistical analysis: Estimated 95% confidence interval of the Cohen's kappa coefficient [61] between Ab responses to the recombinant proteins and MVs are employed. Cohen's kappa coefficient is a classical measure of agreement between two rating systems.

REFERENCES

1. Rylance, J., M. Pai, C. Lienhardt, and P. Garner, *Priorities for tuberculosis research: a systematic review*. Lancet Infect Dis, 2010. 10(12): p. 886-92.
2. Clavijo, E., R. Diaz, A. Anguita, A. Garcia, A. Pinedo, and H. L. Smits, *Comparison of a dipstick assay for detection of Brucella-specific immunoglobulin M antibodies with other tests for serodiagnosis of human brucellosis*. Clin Diagn Lab Immunol, 2003. 10(4): p. 612-5.
3. Ponce, C., E. Ponce, E. Vinelli, A. Montoya, V. de Aguilar, A. Gonzalez, B. Zingales, R. Rangel-Aldao, M. J. Levin, J. Esfandiari, E. S. Umezawa, A. O. Luquetti, and J. F. da Silveira, *Validation of a rapid and reliable test for diagnosis of chagas' disease by detection of Trypanosoma cruzi-specific antibodies in blood of donors and patients in Central America*. J Clin Microbiol, 2005. 43(10): p. 5065-8.
4. Smits, H. L., C. K. Eapen, S. Sugathan, M. Kuriakose, M. H. Gasem, C. Yersin, D. Sasaki, B. Pujianto, M. Vestering, T. H. Abdoel, and G. C. Gussenhoven, *Lateral-flow assay for rapid serodiagnosis of human leptospirosis*. Clin Diagn Lab Immunol, 2001. 8(1): p. 166-9.
5. Steingart, K. R., L. L. Flores, N. Dendukuri, I. Schiller, S. Laal, A. Ramsay, P. C. Hopewell, and M. Pai, *Commercial serological tests for the diagnosis of active pulmonary and extrapulmonary tuberculosis: an updated systematic review and meta-analysis*. PLoS Med, 2011. 8(8): p. e1001062.
6. Steingart, K. R., M. Henry, S. Laal, P. C. Hopewell, A. Ramsay, D. Menzies, J. Cunningham, K. Weldingh, and M. Pai, *A systematic review of commercial serological antibody detection tests for the diagnosis of extrapulmonary tuberculosis*. Postgrad Med J, 2007. 83(985): p. 705-12.
7. Steingart, K. R., M. Henry, S. Laal, P. C. Hopewell, A. Ramsay, D. Menzies, J. Cunningham, K. Weldingh, and M. Pai, *Commercial serological antibody detection tests for the diagnosis of pulmonary tuberculosis: a systematic review*. PLoS Med, 2007. 4(6): p. e202.
8. Kuehn, M. J. and N. C. Kesty, *Bacterial outer membrane vesicles and the host-pathogen interaction*. Genes Dev, 2005. 19(22): p. 2645-55.
9. Beveridge, T. J., *Structures of gram-negative cell walls and their derived membrane vesicles*. J Bacteriol, 1999. 181(16): p. 4725-33.
10. Prados-Rosales, R., A. Baena, L. R. Martinez, J. Luque-Garcia, R. Kalscheuer, U. Veeraraghavan, C. Camara, J. D. Nosanchuk, G. S. Besra, B. Chen, J. Jimenez, A. Glatman-Freedman, W. R. Jacobs, Jr., S. A. Porcelli, and A. Casadevall, *Mycobacteria release active membrane vesicles that modulate immune responses in a TLR2-dependent manner in mice*. J Clin Invest, 2011. 121(4): p. 1471-83.
11. NIH/NIAID. *Tuberculosis Diagnostic Research*. www.niaid.nih.gov/topics/tuberculosis/research/diagnostic/Pages/diagnosis.aspx Mar. 23, 2009

12. World Health Organization, *Global tuberculosis control: WHO report 2011*, 2011: Geneva, Switzerland; www.who.int/tb/publications/global_report/.
13. *Diagnostic Standards and Classification of Tuberculosis in Adults and Children. This official statement of the American Thoracic Society and the Centers for Disease Control and Prevention was adopted by the ATS Board of Directors, July* 1999. This statement was endorsed by the Council of the Infectious Disease Society of America, September 1999. Am J Respir Crit Care Med, 2000. 161(4 Pt 1): p. 1376-95.
14. Boehme, C. C., P. Nabeta, D. Hillemann, M. P. Nicol, S. Shenai, F. Krapp, J. Allen, R. Tahirli, R. Blakemore, R. Rustomjee, A. Milovic, M. Jones, S. M. O'Brien, D. H. Persing, S. Ruesch-Gerdes, E. Gotuzzo, C. Rodrigues, D. Alland, and M. D. Perkins, *Rapid Molecular Detection of Tuberculosis and Rifampin Resistance*. New England Journal of Medicine, 2010. 363(11): p. 1005-1015.
15. Boehme, C. C., M. P. Nicol, P. Nabeta, J. S. Michael, E. Gotuzzo, R. Tahirli, M. T. Gler, R. Blakemore, W. Worodria, C. Gray, L. Huang, T. Caceres, R. Mehdiyev, L. Raymond, A. Whitelaw, K. Sagadevan, H. Alexander, H. Albert, F. Cobelens, H. Cox, D. Alland, and M. D. Perkins, *Feasibility, diagnosticaccuracy, and effectiveness of decentralised use of the Xpert MTB/RIF test for diagnosis of tuberculosis and multidrug resistance: a multicentre implementation study*. Lancet, 2011. 377 (9776): p. 1495-505.
16. Helb, D., M. Jones, E. Story, C. Boehme, E. Wallace, K. Ho, J. Kop, M. R. Owens, R. Rodgers, P. Banada, H. Safi, R. Blakemore, N. T. Lan, E. C. Jones-Lopez, M. Levi, M. Burday, I. Ayakaka, R. D. Mugerwa, B. McMillan, E. Winn-Deen, L. Christel, P. Dailey, M. D. Perkins, D. H. Persing, and D. Alland, *Rapid detection of Mycobacterium tuberculosis and rifampin resistance by use of on-demand, nearpatient technology*. J Clin Microbiol, 2010. 48(1): p. 229-37.
17. Nahid, P., P. S. Kim, C. A. Evans, D. Alland, M. Barer, J. Diefenbach, J. Ellner, R. Hafner, C. D. Hamilton, M. F. Iademarco, G. Ireton, M. E. Kimerling, C. Lienhardt, W. R. MacKenzie, M. Murray, M. D. Perkins, J. E. Posey, T. Roberts, C. Sizemore, W. S. Stevens, L. Via, S. D. Williams, W. W. Yew, and S. Swindells, *Clinical research and development of tuberculosis diagnostics: moving from silos to synergy*. J Infect Dis, 2012. 205 Suppl 2: p. S159-68.
18. Wallis, R. S., M. Pai, D. Menzies, T. M. Doherty, G. Walzl, M. D. Perkins, and A. Zumla, *Biomarkers and diagnostics for tuberculosis: progress, needs, and translation into practice*. Lancet, 2010. 375(9729): p. 1920-37.
19. CDC, *Reported tuberculosis in the United States*, 2008, 2009, US Department of Health and Human Services, CDC: Atlanta, Ga.
20. Steingart, K. R., M. Henry, V. Ng, P. C. Hopewell, A. Ramsay, J. Cunningham, R. Urbanczik, M. Perkins, M. A. Aziz, and M. Pai, *Fluorescence versus conventional sputum smear microscopy for tuberculosis: a systematic review*. Lancet Infect Dis, 2006. 6(9): p. 570-81.
21. 2006 *Annual TB Summary*, 2008, New York City Department of Health and Mental Hygiene, Bureau of Tuberculosis Control: New York, N.Y. p. www.nyc.gov/html/doh/downloads/pdf/tb/tb2006.pdf
22. Achkar, J. M., S. D. Lawn, M. Y. Moosa, C. A. Wright, and V. O. Kasprowicz, *Adjunctive tests for diagnosis of tuberculosis: serology, ELISPOT for site-specific lymphocytes, urinary lipoarabinomannan, string test, and fine needle aspiration*. J Infect Dis, 2011. 204 Suppl 4: p. S1130-41.
23. Lawn, S. D., *Point-of-care detection of lipoarabinomannan (LAM) in urine for diagnosis of HIV associated tuberculosis: a state of the art review*. BMC Infect Dis, 2012. 12(1): p. 103.
24. Lawn, S. D., A. D. Kerkhoff, M. Vogt, and R. Wood, *Diagnostic accuracy of a low-cost, urine antigen, point-of-care screening assay for HIV-associated pulmonary tuberculosis before antiretroviral therapy: a descriptive study*. Lancet Infect Dis, 2012. 12(3): p. 201-9.
25. Lawn, S. D., A. D. Kerkhoff, M. Vogt, and R. Wood, *Clinical significance of lipoarabinomannan (LAM) detection in urine using a low-cost point-of-care diagnostic assay for HIV-associated tuberculosis*. AIDS, 2012.
26. Diel, R., D. Goletti, G. Ferrara, G. Bothamley, D. Cirillo, B. Kampmann, C. Lange, M. Losi, R. Markova, G. B. Migliori, A. Nienhaus, M. Ruhwald, D. Wagner, J. P. Zellweger, E. Huitric, A. Sandgren, and D. Manissero, *Interferon-gamma release assays for the diagnosis of latent Mycobacterium tuberculosis infection: a systematic review and meta-analysis*. Eur Respir J, 2011. 37(1): p. 88-99.
27. Menzies, D., M. Pai, and G. Comstock, *Meta-analysis: new tests for the diagnosis of latent tuberculosis infection: areas of uncertainty and recommendations for research*. Ann Intern Med, 2007. 146(5): p. 340-54.
28. Steingart, K. R., N. Dendukuri, M. Henry, I. Schiller, P. Nahid, P. C. Hopewell, A. Ramsay, M. Pai, and S. Laal, *Performance of purified antigens for serodiagnosis of pulmonary tuberculosis: a meta-analysis*. Clin Vaccine Immunol, 2009. 16(2): p. 260-76.
29. Achkar, J. M., E. Jenny-Avital, X. Yu, S. Burger, E. Leibert, P. W. Bilder, S. C. Almo, A. Casadevall, and S. Laal, *Antibodies against immunodominant antigens of Mycobacterium tuberculosis in subjects with suspected tuberculosis in the United States compared by HIV status*. Clin Vaccine Immunol, 2010. 17(3): p. 384-92.
30. Yu, X., R. Prados-Rosales, E. R. Jenny-Avital, K. Sosa, A. Casadevall, and J. M. Achkar, *Comparative evaluation of profiles of antibodies to mycobacterial capsular polysaccharides in tuberculosis patients and controls stratified by HIV status*. Clin Vaccine Immunol, 2012. 19(2): p. 198-208.
31. Morris, K., *WHO recommends against inaccurate tuberculosis tests*. Lancet, 2011. 377(9760): p. 113-4.
32. Keenan, J. I., S. G. Rijpkema, Z. Durrani, and J. A. Roake, *Differences in immunogenicity and protection in mice and guinea pigs following intranasal immunization with Helicobacter pylori outer membrane antigens*. FEMS Immunol Med Microbiol, 2003. 36(3): p. 199-205.
33. Alaniz, R. C., B. L. Deatherage, J. C. Lara, and B. T. Cookson, *Membrane vesicles are immunogenic facsimiles of Salmonella typhimurium that potently activate dendritic cells, prime B and T cell responses, and stimulate protective immunity in vivo*. J Immunol, 2007. 179(11): p. 7692-701.
34. Schild, S., E. J. Nelson, and A. Camilli, *Immunization with Vibrio cholerae outer membrane vesicles induces protective immunity in mice*. Infect Immun, 2008. 76(10): p. 4554-63.
35. McConnell, M. J., C. Rumbo, G. Bou, and J. Pachon, *Outer membrane vesicles as an acellular vaccine against Acinetobacter baumannii*. Vaccine, 2011. 29(34): p. 5705-10.

36. Rivera, J., R. J. Cordero, A. S. Nakouzi, S. Frases, A. Nicola, and A. Casadevall, *Bacillus anthraces produces membrane-derived vesicles containing biologically active toxins.* Proc Natl Acad Sci USA, 2010. 107(44): p. 19002-7.
37. Nieves, W., S. Asakrah, O. Qazi, K. A. Brown, J. Kurtz, D. P. Aucoin, J. B. McLachlan, C. J. Roy, and L. A. Morici, *A naturally derived outer-membrane vesicle vaccine protects against lethal pulmonary Burkholderia pseudomallei infection.* Vaccine, 2011. 29(46): p. 8381-9.
38. Camacho, A. I., J. de Souza, S. Sanchez-Gomez, M. Pardo-Ros, J. M. Irache, and C. Gamazo, *Mucosal immunization with Shigella flexneri outer membrane vesicles induced protection in mice.* Vaccine, 2011. 29(46): p. 8222-9.
39. Jackson, C., D. Lennon, S. Wong, J. Yan, J. Stewart, S. Reid, P. Oster, E. Ypma, and D. Martin, *Antibody persistence following MeNZB vaccination of adults and children and response to a fourth dose in toddlers.* Arch Dis Child, 2011. 96(8): p. 744-51.
40. Nokleby, H., P. Aavitsland, J. O'Hallahan, B. Feiring, S. Tilman, and P. Oster, *Safety review: two outer membrane vesicle (OMV) vaccines against systemic Neisseria meningitidis serogroup B disease.* Vaccine, 2007. 25(16): p. 3080-4.
41. Wedege, E., K. Bolstad, A. Aase, T. K. Herstad, L. McCallum, E. Rosenqvist, P. Oster, and D. Martin, *Functional and specific antibody responses in adult volunteers in new Zealand who were given one of two different meningococcal serogroup B outer membrane vesicle vaccines.* Clinical and Vaccine Immunology, 2007. 14(7): p. 830-838.
42. Kunnath-Velayudhan, S., H. Salamon, H. Y. Wang, A. L. Davidow, D. M. Molina, V. T. Huynh, D. M. Cirillo, G. Michel, E. A. Talbot, M. D. Perkins, P. L. Feigner, X. Liang, and M. L. Gennaro, *Dynamic antibody responses to the Mycobacterium tuberculosis proteome.* Proc Natl Acad Sci USA, 2010. 107(33): p. 14703-8.
43. Lyashchenko, K., R. Colangeli, M. Houde, H. Al Jahdali, D. Menzies, and M. L. Gennaro, *Heterogeneous antibody responses in tuberculosis.* Infect Immun, 1998. 66(8): p. 3936-40.
44. Lyashchenko, K. P., M. Singh, R. Colangeli, and M. L. Gennaro, *A multi-antigen print immunoassay for the development of serological diagnosis of infectious diseases.* J Immunol Methods, 2000. 242(1-2): p. 91-100.
45. Lijmer, J. G., B. W. Mol, S. Heisterkamp, G. J. Bonsel, M. H. Prins, J. H. van der Meulen, and P. M. Bossuyt, *Empirical evidence of design-related bias in studies of diagnostic tests.* Jama, 1999. 282(11): p. 1061-6.
46. Rutjes, A. W., J. B. Reitsma, M. Di Nisio, N. Smidt, J. C. van Rijn, and P. M. Bossuyt, *Evidence of bias and variation in diagnostic accuracy studies.* CMAJ, 2006. 174(4): p. 469-76
47. *Diagnosis and treatment of disease caused by nontuberculous mycobacteria. This official statement of the American Thoracic Society was approved by the Board of Directors, March* 1997. Medical Section of the American Lung Association. Am J Respir Crit Care Med, 1997. 156(2 Pt 2): p. S1-25.
48. Laemmli, U. K., *Cleavage of structural proteins during the assembly of the head of bacteriophage T4.* Nature, 1970. 227(5259): p. 680-5.
49. Deeg, C. A., A. J. Raith, B. Amann, J. W. Crabb, S. R. Thurau, S. M. Hauck, M. Ueffing, G. Wildner, and M. Stangassinger, *CRALBP is a highly prevalent autoantigen for human autoimmune uveitis.* Clin Dev Immunol, 2007. 2007: p. 39245.
50. Shimazaki, K., G. V. Jirawuthiworavong, J. R. Heckenlively, and L. K. Gordon, *Frequency of anti-retinal antibodies in normal human serum.* J Neuroophthalmol, 2008. 28(1): p. 5-11.
51. Clopper, C. J. and E. S. Pearson, *The use of confidence or fiducial limits illustrated in the case of the binomial.* Biometrika, 1934(26): p. 404-413.
52. Chow, S. C., J. Shao, and H. Wang, *Sample Size Calculations in Clinical Research*2003, New York: Marcel Dekker.
53. Fleiss, J. L., B. Levin, and M. C. Paik, *Statistical Methods for Rates and Proportions,* ed. T. Edition2003, New York: John Wiley & Sons.
54. Yera, H., S. Andiva, C. Perret, D. Limonne, P. Boireau, and J. Dupouy-Camet, *Development and evaluation of a Western blot kit for diagnosis of human trichinellosis.* Clin Diagn Lab Immunol, 2003. 10(5): p. 793-6.
55. Engstrom, S. M., E. Shoop, and R. C. Johnson, *Immunoblot interpretation criteria for serodiagnosis of early Lyme disease.* J Clin Microbiol, 1995. 33(2): p. 419-27.
56. O'Farrell, P. H., *High resolution two-dimensional electrophoresis of proteins.* J Biol Chem, 1975. 250(10): p. 4007-21.
57. Simula, M. P., A. Notarpietro, G. Toffoli, and V. D. Re, *2-D gel electrophoresis: constructing 2D-gel proteome reference maps.* Methods Mol Biol, 2012. 815: p. 163-73.
58. Wilm, M., G. Neubauer, and M. Mann, *Parent ion scans of unseparated peptide mixtures.* Anal Chem, 1996. 68(3): p. 527-33.
59. Aslanidis, C. and P. J. de Jong, *Ligation-independent cloning of PCR products (LIC-PCR).* Nucleic Acids Res, 1990. 18(20): p. 6069-74.
60. Sauder, M. J., M. E. Rutter, K. Bain, I. Rooney, T. Gheyi, S. Atwell, D. A. Thompson, S. Emtage, and S. K. Burley, *High throughput protein production and crystallization at NYSGXRC.* Methods Mol Biol, 2008. 426: p. 561-75.
61. Cohen, J., *A coefficient of agreement for nominal scales.* Educational and Psychological measurement, 1960. 20(1): p. 37-46.
62. Newcombe, R. G., *Two-sided confidence intervals for the single proportion: comparison of seven methods.* Stat Med, 1998. 17(8): p. 857-72.
63. Falkinham, J. O., 3rd, *Epidemiology of infection by nontuberculous mycobacteria.* Clin Microbiol Rev, 1996. 9(2): p. 177-215.
64. Morrissey, A. B., T. O. Aisu, J. O. Falkinham, 3rd, P. P. Eriki, J. J. Ellner, and T. M. Daniel, *Absence of Mycobacterium avium complex disease in patients with AIDS in Uganda.* J Acquir Immune Defic Syndr, 1992. 5(5): p. 477-8.
65. Okello, D. O., N. Sewankambo, R. Goodgame, T. O. Aisu, M. Kwezi, A. Morrissey, and J. J. Ellner, *Absence of bacteremia with Mycobacterium avium-intracellulare in Ugandan patients with AIDS.* J Infect Dis, 1990. 162(1): p. 208-10.

What is claimed:

1. A method of detecting active Tuberculosis disease in a subject comprising contacting a sample from the subject with a first agent capable of binding an IgG, IgA and/or IgM directed to a first protein or proteins each having a MW of about 36 kDa in or on a *Mycobacterium tuberculosis* membrane vesicle or a *Bacillus* Calmette-Guérin (BCG) membrane vesicle, a second agent capable of binding an IgG, IgA and/or IgM directed to a second protein or proteins each having a MW of about 25 kDa in or on a *Mycobacterium tuberculosis* membrane vesicle or a BCG membrane vesicle, and a third agent capable of binding an IgG, IgA and/or IgM directed to a third protein or proteins each having a MW of about 23 kDa in or on a *Mycobacterium tuberculosis* membrane vesicle or a BCG membrane vesicle, wherein the protein or proteins having a MW of about 36 kDa is selected from the group consisting of secreted antigen 85-B, serine protease PepA, protein MB3832c, secreted antigen 85-A FBPA, protein Mb0822c, protein RV0799c, antigen 85-c, Fe(III) dicitrate binding periplasmic lipoprotein, protein Mb3759, pstS1 (Rv0934), and ald (Rv2780), wherein the protein or proteins having a MW of about 25 kDa is selected from the group consisting of protein Mb2554c, protein MPT64, lipoprotein LprA, protein RV3717, putative secreted protein, lipoprotein LprG (Rv1411), and lipoprotein LppX (Rv2945), wherein the protein having a MW of about 23 kDa is selected from the group consisting of protein lipoprotein LpqN, 30S ribosomal protein S4, thioredoxin protein, rplD, (Rv0702), rpsD (Rv3458), HBHA (Rv0475), and LprI (Rv 1541), and wherein detection of the presence of IgG, IgA and/or IgM directed to the first protein or proteins, the second protein or proteins, and the third protein or proteins present in or on the membrane vesicle indicates active Tuberculosis disease in the subject.

2. The method of claim 1, wherein active Tuberculosis disease is not caused by a drug-resistant *Mycobacterium tuberculosis* infection.

3. The method of claim 1, further comprising administering to a subject found to have active Tuberculosis disease by the method, a therapeutically effective amount of one or more anti-tuberculosis medications.

4. The method of claim 3, wherein the anti-tuberculosis-medication comprises one or more of isoniazid, rifampicin, pyrazinamide, and ethambutol.

5. The method of claim 3, wherein the anti-tuberculosis-medication comprises one or more of an aminoglycoside, capreomycin, viomycin, enviomycin, a fluoroquinolones, a thioamide, a cycloserine and terizidone.

6. The method of claim 1, wherein the first agent consists of an isolated protein that is secreted antigen 85-B, serine protease PepA, protein MB3832c, secreted antigen 85-A FBPA, protein Mb0822c, protein RV0799c, antigen 85-c, Fe(III) dicitrate binding periplasmic lipoprotein, protein Mb3759, pstS1 (Rv0934), or ald (Rv2780).

7. The method of claim 1, wherein the second agent consists of an isolated protein that is protein Mb2554c, protein MPT64, lipoprotein LprA, protein RV3717, putative secreted protein, lipoprotein LprG (Rv1411), or lipoprotein LppX (Rv2945).

8. The method of claim 1, wherein the third agent consists of an isolated protein that is protein lipoprotein LpqN, 30S ribosomal protein S4, thioredoxin protein, rplD, (Rv0702), rpsD (Rv3458), HBHA (Rv0475), or LprI (Rv 1541).

9. The method of claim 1, wherein the sample consists of serum, plasma or whole blood.

10. The method of claim 1, wherein the first agent, the second agent and the third agent are each detectably labeled.

11. The method of claim 1, wherein the IgG, IgA or IgM is determined to be present by detection of a detectable label of the first agent, the second agent or the third agent bound to the IgG, IgA or IgM.

12. The method of claim 1, wherein the subject is a human.

13. The method of claim 1, wherein the one or more proteins are present in or on a *Mycobacterium tuberculosis* membrane vesicle.

14. The method of claim 1, wherein the one or more proteins are present in or on a BCG membrane vesicle.

* * * * *